«12» United States Patent
Kim et al.

(10) Patent No.: US 10,639,397 B2
(45) Date of Patent: May 5, 2020

(54) PARTIAL SKULL REPLACEMENTS CAPABLE OF MONITORING IN REAL TIME AND DELIVERING SUBSTANCES INTO BRAIN TISSUE, AND USES THEREOF

(71) Applicants: RESEARCH & BUSINESS FOUNDATION SUNGKYUNKWAN UNIVERSITY, Suwon-si (KR); INSTITUTE FOR BASIC SCIENCE, Daejeon (KR)

(72) Inventors: Seong-Gi Kim, Suwon-si (KR); Minah Suh, Seoul (KR); Chaejeong Heo, Suwon-si (KR); Hyoung Won Baac, Anyang-si (KR)

(73) Assignees: Research & Business Foundation Sungkyunkwan University, Suwon-si (KR); Institute for Basic Science, Daejeon (KR)

( * ) Notice: Subject to any disclaimer, the term of this patent is extended or adjusted under 35 U.S.C. 154(b) by 623 days.

(21) Appl. No.: 15/068,051

(22) Filed: Mar. 11, 2016

(65) Prior Publication Data

US 2016/0263277 A1 Sep. 15, 2016

(30) Foreign Application Priority Data

Mar. 12, 2015 (KR) .................. 10-2015-0034628

(51) Int. Cl.
*A61L 27/18* (2006.01)
*A61B 5/00* (2006.01)
(Continued)

(52) U.S. Cl.
CPC ............ *A61L 27/18* (2013.01); *A61B 5/6864* (2013.01); *A61B 5/6868* (2013.01);
(Continued)

(58) Field of Classification Search
CPC ..... A61L 27/18; A61B 5/6864; A61B 5/6868; A61B 5/0084; A61B 5/6848; A61B 8/00;
(Continued)

(56) References Cited

FOREIGN PATENT DOCUMENTS

KR     10-2011-0115074 A     10/2011

OTHER PUBLICATIONS

Dural substitute for long-term imaging of cortical activity in behaving monkeys and its clinical implications by Arieli et al.; pub. Journal of Neuroscience Methods 114 (2002); pp. 119-133.*
A Passive Refillable Intraocular MEMS Drug Delivery Device by Lo et al; pub. Proceedings of 2006 International Conference on Microtechnologies in Medicine and Biology Okinawa, Japan May 9-12, 2006; pp. 74-77.*

(Continued)

*Primary Examiner* — Katherine L Fernandez
*Assistant Examiner* — Michael S Kellogg
(74) *Attorney, Agent, or Firm* — NSIP Law

(57) ABSTRACT

The present invention relates to a partial skull replacement consisting of polydimethylsiloxane (PDMS) and a method of monitoring biological tissues within a skull using the partial skull replacement. The method of monitoring using the partial skull replacement of the present invention has a minimal influence on intracranial pressure and cerebrospinal fluid flow as compared to a conventional cranial window technique using glass, and, by way of visualizing biological tissues within a skull with enhanced clarity, is expected to be usefully employed as a method of monitoring biological tissues within the skull.

10 Claims, 10 Drawing Sheets

(51) Int. Cl.
*A61K 49/22* (2006.01)
*A61K 49/00* (2006.01)
*A61B 5/04* (2006.01)
*A61B 8/00* (2006.01)
*A61B 5/026* (2006.01)

(52) U.S. Cl.
CPC ........ *A61K 49/0045* (2013.01); *A61K 49/226* (2013.01); *A61B 5/0042* (2013.01); *A61B 5/0068* (2013.01); *A61B 5/0071* (2013.01); *A61B 5/0084* (2013.01); *A61B 5/0095* (2013.01); *A61B 5/0261* (2013.01); *A61B 5/04001* (2013.01); *A61B 5/4094* (2013.01); *A61B 5/6848* (2013.01); *A61B 8/00* (2013.01); *A61M 2210/0687* (2013.01)

(58) Field of Classification Search
CPC ... A61B 5/0042; A61B 5/0261; A61B 5/0068; A61B 5/0071; A61B 5/4094; A61B 5/0095; A61B 5/04001; A61K 49/0045; A61K 49/226; A61M 2210/0687
See application file for complete search history.

(56) References Cited

OTHER PUBLICATIONS

Amos, Arieli, et al."*Dural substitute for long-term imaging of cortical activity in behaving monkeys and its clinical implications.*" Journal of neuroscience methods 114.2 (2002): 119-133. (15 pages in English).

Slovin, Hamutal, et al. "*Long-term voltage-sensitive dye imaging reveals cortical dynamics in behaving monkeys.*" Journal of neurophysiology 88.6 (2002) (19 pages in English).

Tsou, Jean, et al. "*Role of ultrasonic shear rate estimation errors in assessing inflammatory response and vascular risk.*" Ultrasound in medicine & biology 34.6 (2008) (22 pages in English).

Yang, Guang, et al. "*Thinned-skull cranial window technique for long-term imaging of the cortex in live mice.*" Nature protocols 5.2 (2010) (8 pages in English).

Shih, Andy, et al. "*A polished and reinforced thinned-skull window for long-term imaging of the mouse brain.*" JoVE (Journal of Visualized Experiments) 61 (2012): e3742-e3742. (6 pages in English).

* cited by examiner

PARTIAL SKULL REPLACEMENTS CAPABLE OF MONITORING IN REAL TIME AND DELIVERING SUBSTANCES INTO BRAIN TISSUE, AND USES THEREOF

CROSS-REFERENCE TO RELATED APPLICATION

This application claims priority to and the benefit of Korean Patent Application No. 10-2015-0034628, filed on Mar. 12, 2015, the disclosure of which is incorporated herein by reference in its entirety.

The present invention was made with the support of the Integrated Research of Basic Neuroscience and Biophysics # S-2014-1974-000-1 of the Institute for Basic Science (IBS).

BACKGROUND

1. Field of the Invention

The present invention relates to a partial skull replacement consisting of polydimethylsiloxane (PDMS) and a method of using the same for monitoring biological tissue within a skull or injecting an agent.

2. Discussion of Related Art

A skull is a set of bones constituting the skeletal structure of a head and serves to hold a brain therein, giving protection for the same, and provides a space for sense organs such as eyes, ears, a nose, and a mouth. Being part of the skeleton in closest proximity to the brain, the skull may have an influence on the flow of cerebrospinal fluid (CSF) and is a structure that requires an access for surgery or for the real-time monitoring of blood vessels and tissue in the brain.

In the meantime, an artificial bone is a substitute used to take the role of an existing bone that can no longer carry out the role of a bone, such as a supporting function, due to severe damage. Initially, such an artificial bone was developed using materials that were biologically inert, resulting in limited applications thereof due to the infection or inflammation of a surrounding tissue. However, with the designing and development of materials that are biocompatible, rather than bioinert, in line with today's rapid development of biomaterials technology involving metals, ceramics, and polymers, artificial bones are developed variously depending on an area of application and an intended use. In other words, artificial bone materials having durability appropriate for the area of application and being capable of combining sufficiently with existing tissues without causing an additional immune response are being studied. In addition, a metal-based substitute such as a cobalt-chromium alloy (Co—Cr alloy) and a titanium alloy (Ti alloy); a biodegradable polymer substitute such as poly(lactic-co-glycolic) acid (PLGA), poly(glycolic acid) (PGA), and poly(lactic acid) (PLA); a ceramic substitute such as alumina, titania, and calcium phosphate, and the like are currently in use for the production of an artificial bone (Korean Laid-open Patent Application No. 10-2011-0115074).

Hereupon, the present inventors combined the artificial-bone-related technology with the monitoring of biological tissues within the skull to observe, through the artificial bone, the changes in cerebral blood flow, neural tissue functionality, and the like within the skull in real time. In particular, when the skull is replaced with a conventional glass material, which makes a brittle substitute, delivering a substance through the substitute is impossible and long-term monitoring, which may induce a change in the CSF flow by applying pressure onto the brain because of rigidity of glass, is difficult to accomplish. In addition, in order to perform the monitoring of the interior through the partial skull replacement, the use of a material with high optical transparency and high ultrasonic transmittance is required. Therefore, there is a need for the development of a partial skull replacement based on an elastic and transparent material having excellent biocompatibility and an ability to deliver a foreign substance therethrough and inducing a minimal change in the CSF flow surrounding the brain.

SUMMARY OF THE INVENTION

The present invention, which was made to solve the aforementioned problems, was completed based on the confirmation by the present inventors that the use of a partial skull replacement consisting of polydimethylsiloxane (PDMS) with a proper implantation technique in a skull enabled the long-term monitoring of biological tissues within the skull in real time and the direct and repetitive administering of an agent.

Hereupon, the present invention is directed to providing a partial skull replacement that consists of PDMS and replaces a part of a skull to visualize biological tissues within the skull or deliver a foreign substance to the brain tissues.

In addition, the present invention is directed to providing a method of installing a window in a skull, wherein the method includes removing the skull in a target site; and disposing a partial skull replacement consisting of PDMS in the area from which the skull was removed.

Additionally, the present invention is directed to providing a method of monitoring biological tissues within a skull, wherein the method includes removing the skull in an area to be monitored; disposing a partial skull replacement consisting of PDMS in the area from which the skull was removed; and monitoring the biological tissues within the skull through the disposed partial skull replacement.

Moreover, the present invention is directed to providing a method of injecting an agent into a skull, wherein the method includes removing the skull in an area of injection; disposing a partial skull replacement consisting of PDMS in the area from which the skull was removed; penetrating the partial skull replacement with an injection tool; and injecting the agent into the tissue via the penetrated injection tool.

Furthermore, the present invention is directed to a method of skull replacement surgery, wherein the method includes disposing a partial skull replacement consisting of PDMS in the area from which the skull was removed.

However, the technical objectives of the present invention are not limited to those mentioned above, and other objectives not addressed herein will be clearly understood by those skilled in the art from the following descriptions.

In order to achieve the aforementioned objectives of the present invention, the present invention provides a partial skull replacement that consists of PDMS and replaces a part of a skull to visualize biological tissues within the skull or deliver a foreign substance to the brain tissues.

In one embodiment of the present invention, the biological tissues within the skull may include cerebral blood vessels, brain cells, and the like.

The present invention provides a method of preparing a window in a skull, wherein the method includes removing the skull in a target site; and disposing a partial skull replacement consisting of PDMS in the area from which the skull was removed.

In one embodiment of the present invention, the partial skull replacement enables, by replacing a part of the skull, the visualization of blood vessels and tissues or the delivery of a foreign substance into the biological tissues.

In addition, the present invention provides a method of monitoring biological tissues within a skull, wherein the method includes removing the skull from an area to be monitored; disposing a partial skull replacement consisting of PDMS in the area from which the skull was removed; and monitoring the biological tissues within the skull through the disposed partial skull replacement.

In one embodiment of the present invention, the partial skull replacement may enable the long-term monitoring of brain tissues within the skull by maintaining intracranial pressure and cerebrospinal fluid (CSF) flow within the skull.

In another embodiment of the present invention, the monitoring can be carried out using a mechanical neuromodulation such as laser or ultrasound.

In addition, the present invention provides a method of injecting an agent into a skull, wherein the method includes removing the skull in an area of injection; disposing a partial skull replacement consisting of PDMS in the area from which the skull was removed; penetrating the partial skull replacement with an injection tool; and injecting the agent into the skull via the penetrated injection tool.

In one embodiment of the present invention, the agent may be a lesion inducer, a therapeutic agent, a treatment promoter, a diagnostic agent, or an imaging agent.

In another embodiment of the present invention, the injection tool may be a pipette or a needle.

In addition, the present invention provides a method of skull replacement surgery, wherein the method includes disposing a partial skull replacement consisting of PDMS in the area from which the skull was removed.

The partial skull replacement of the present invention includes PDMS as an active ingredient, and, besides visualizing brain tissues more clearly compared to a conventional cranial window technique using glass, has been recognized to be able to keep the brain healthy by having a minimal influence on intracranial pressure and CSF flow, allow the insertion of a pipette, etc. for the repetitive and simultaneous injection of a drug into brain tissues and for the measurement of brain signals, and enable ultrasonic penetration for the monitoring of brain tissues. Therefore, it is expected that the partial skull replacement of the present invention can be usefully employed in various methods of monitoring biological tissues within the skull.

In addition, in the case of the conventional windows based on glass, the delivery of ultrasound was very difficult to achieve because of high ultrasonic attenuation through the glass and a large difference in acoustic impedance with the CSF and biological tissues. However, the PDMS partial skull replacement of the present invention offers an easy delivery of ultrasound, since the difference in acoustic impedance is very small and the ultrasonic attenuation of the material itself is significantly lower than that of glass. Therefore, the existing ultrasound system combined with the PDMS partial skull replacement of the present invention is expected to be useful in the exploration of new areas such as the use of ultrasonic in the long-term imaging of tissues within the skull and for therapeutic applications and have an increased clinical utility.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
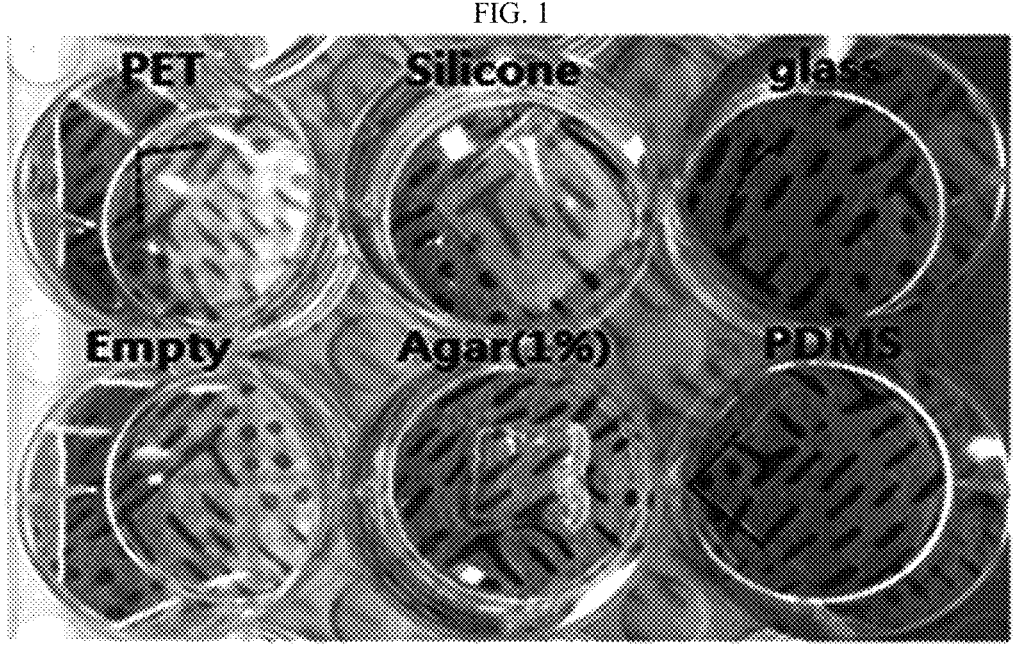
FIG. 1 is an image showing the transparency of candidate materials (glass, agarose (1% concentration), silicone, polyethylene terephthalate (PET), and polydimethylsiloxane (PDMS)) for a partial skull replacement when observed by the naked eye.

Based on the excellent transparency, hydrophobicity, and elastic of polydimethylsiloxane (PDMS), the present inventors devised a partial skull replacement consisting of PDMS and a method of implanting the same into a skull, and completed the present invention based on the fact that the partial skull replacement and the method enabled the long-term visualization of brain tissues within the skull in real time by maintaining intracranial pressure and cerebrospinal fluid (CSF) flow, and the monitoring of brain functions by allowing the penetration of various foreign agents (substances) and ultrasound.

Hereinafter, the present invention will be described in detail.

The present invention provides a partial skull replacement consisting of PDMS and, by replacing a part of the skull, visualization of biological tissues within the skull or delivery of a foreign substance into the biological tissues.

In addition, the present invention provides a method of preparing a window in the skull, wherein the method includes removing the skull in a target site; and disposing a partial skull replacement consisting of PDMS in the area from which the skull was removed.

The term "partial skull replacement" used herein refers to a material replacing a part of a skull bone. For the objectives of the present invention, besides consisting of a biocompatible material, a partial skull replacement is necessarily a transparent material for the visualization of brain within the skull and needs to consist of a soft material so that the penetration of ultrasound, a glass pipette, and the like is possible.

Conventionally, a cranial window technique, in which a part of a skull is removed and the area is covered with glass, has been used as a method of visualizing biological tissues within the skull, but such a method affects intracranial pressure, thus making long-term monitoring difficult to achieve. Not only that, since the final structure is a closed structure enclosed by a glass cover, it is difficult to make an insertion through the hard and highly brittle glass for the installation of an additional electrode and the direct injection of a brain signal measuring device or a drug. Hence, to solve such problems, the present inventors prepared a window by producing a partial skull replacement consisting of PDMS and disposing the same in place of a removed part of the skull. Therefore, the final structure of the produced window is a flexible structure in which only PDMS, without an additional device or material (e.g. glass), is used, which makes the structure capable of being bent, expanded, or allowing an insertion/penetration without constraint. Hence, besides enabling the delivery of various agents such as drugs or proteins into the brain within the skull, the partial skull replacement of the present invention can enable the real-time monitoring of changes in brain tissues within the skull due to the high light transmittance and high ultrasonic transmittance of PDMS.

Examples of biological tissues within a skull to be monitored through the present invention include brain tissue and blood vessels in the brain. Such biological tissues are preferably, but are not limited to, cerebral blood vessels, neurons or glial cells.

In one exemplary embodiment of the present invention, PDMS, among the candidate materials for a partial skull replacement, was found to have low cytotoxicity and high transparency. Hence, an artificial partial skull replacement consisting of PDMS was produced and attached to the skull of an living rat to prepare a final window consisting only of a PDMS attachment (see Examples 1 and 2).

In another exemplary embodiment of the present invention, the use of an attached artificial partial skull replacement of the present invention enabled the visualization of cerebral cortex up to as much as 10 weeks to 15 weeks after the attaching of the partial skull replacement and the observation of the brain with high clarity. In addition, that the use of the attached artificial partial skull replacement of the present invention did not cause an influence on cerebrospinal fluid (CSF) flow and intracranial pressure as compared to conventional glass/agar was confirmed in detail by simulation, and the high ultrasonic transmittance of the material itself was also confirmed (see Example 3).

Therefore, the partial skull replacement consisting of PDMS can be usefully employed for monitoring biological tissues within a skull.

Hence, in another aspect of the present invention, the present invention provides a method of monitoring biological tissues within a skull, wherein the method includes removing the skull in an area to be monitored; disposing a partial skull replacement consisting of PDMS in the area from which the skull was removed; and monitoring the biological tissues within the skull through the disposed partial skull replacement.

In other words, by preparing a window using PDMS, the monitoring method of the present invention can visualize brain tissue with improved clarity, have a minimal influence on CSF flow and maintain intracranial pressure at a constant level, keeping the brain healthy, and thus, enabling long-term monitoring.

In still another exemplary embodiment of the present invention, it was confirmed that the use of the attached artificial partial skull replacement of the present invention enables the repetitive and direct administration of various agents such as drugs or proteins, which makes the attached artificial partial skull replacement of the present invention usable for the imaging of brain tissue or changes in brain tissue functionality (see Example 4).

Thus, it is advantageous to prepare a window by disposing a partial skull replacement consisting of PDMS in a part of the skull, as the partial skull replacement enables the direct and repetitive administration of various foreign substances for the monitoring of brain, treatment, or the like into tissues.

Hence, in still another aspect of the present invention, the present invention provides a method of injecting an agent into the skull, wherein the method includes removing the skull in an area of injection; disposing a partial skull replacement consisting of PDMS in the area from which the skull was removed; penetrating the partial skull replacement with an injection tool; and injecting the agent into the skull via the penetrated injection tool.

As used herein, the term "agent" refers to a foreign substance that can be administered to diagnose tissues in a living body or induce, treat, or facilitate the treatment of a lesion. For example, the term "agent" may refer to a biochemical substance such as a protein or a drug, but is not limited thereto.

In the present invention, the injection tool for injecting the agent is preferably, but is not limited to, a pipette or a needle.

Hereinafter, exemplary examples of the invention will be described for promoting an understanding of the invention. However, the following examples should be considered in a descriptive sense only and the scope of the invention is not limited to the following examples.

Example 1

Search for Skull Substitute Material 1-1. Preparation of Substitute Materials

First, the present inventors searched for a material for a partial skull replacement for long-term monitoring of a surface of the brain within the skull. For this, glass, agarose (at 1% concentration), silicone, polyethylene terephthalate (PET), and PDMS were selected as candidate materials for a partial skull replacement and were each prepared in a cell culture dish (FIG. 1). Later, the cytotoxicity, hydrophilicity, and transparency of the materials were compared and evaluated.

1-2. Evaluation of Cytotoxicity

In preparation for an application into biological tissue, the cytotoxicity of the candidate materials for a partial skull replacement prepared in Example 1-1 were evaluated. Specifically, SH-SY5Y cells, which are the human neuroblastoma cell lines, were cultured in cell culture dishes, each of which was treated with each candidate material for a partial skull replacement. 24 hours later, the cell viability was calculated, and the cell proliferation forms were observed under an optical microscope.

Figure 2:
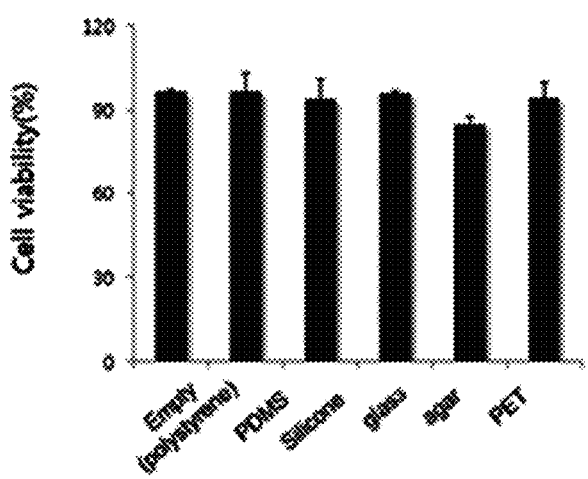
FIG. 2 shows the results of determining, for each candidate material for a partial skull replacement, (A) cell viability; and (B) the cell proliferation (provided in optical images), both of which were obtained 24 hours after the treatment of the materials.
Figure 2:
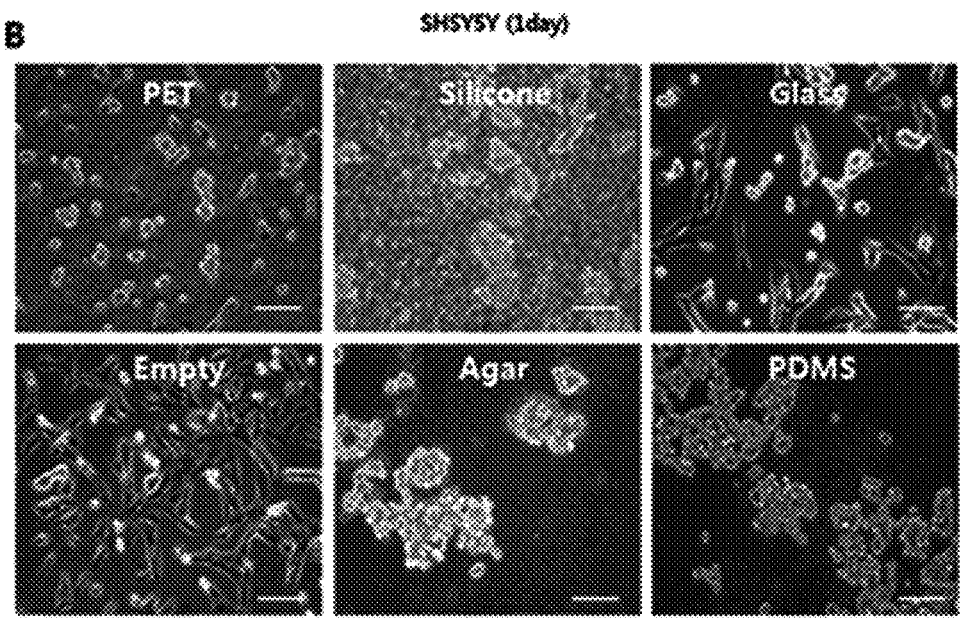

The results show that, as shown in FIG. 2, agar measured the lowest degree of cell viability, approximately 80%, among all skull replacement materials, and the other materials measured a high degree of cell viability, 90% or more. In addition, cells were found to proliferate while being attached to glass and an empty culture dish, whereas with silicone, agarose, PDMS, and PET, the cells proliferated relatively away from the materials, while only a relatively small number of cells were seen as proliferating while being attached to the materials.

1-3. Evaluation of Hydrophilicity and Transparency

When a skull replacement material is actually used to prepare a window, the excellent transparency of the skull replacement material is required for the monitoring of biological tissues through the skull replacement material. In addition, the hydrophobicity of the substitute material is beneficial for maintaining such transparency. More specifically, when the skull replacement material is more hydrophilic rather than hydrophobic, it is likely that cells and other proteins adhere to the material, and dura mater that was removed may also rapidly proliferate thereon, causing the transparency of the window to be reduced gradually with a long-term use of the window. For this reason, the hydrophilicity and transparency of the candidate materials for a partial skull replacement, which were prepared in Example 1-1, were evaluated.

Figure 3:
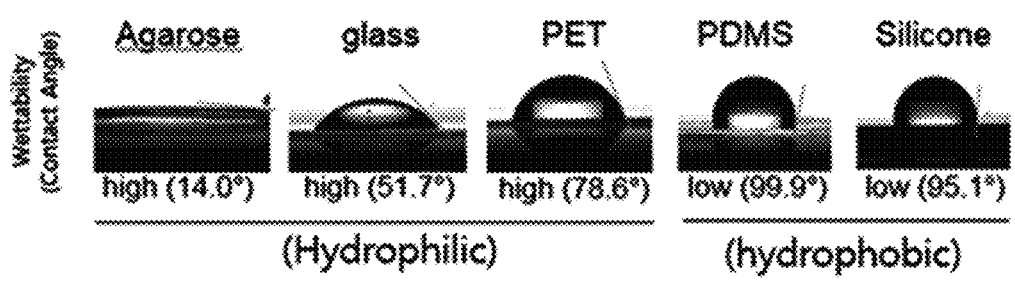
FIG. 3 shows the results of determining, for each candidate material for a partial skull replacement, (A) the contact angle at an interface between a surface of the material and a water drop; and (B) the hydrophilicity/hydrophobicity characteristic of the material evaluated based on the contact angle.
Figure 3:
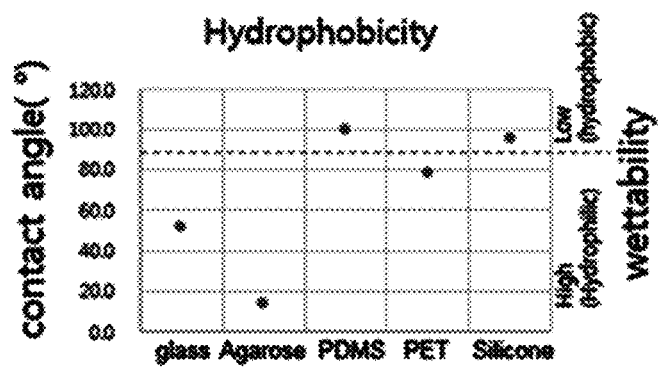

More specifically, the hydrophilicity was determined by applying a water drop on a surface of the materials of interest and subsequently measuring the contact angle between the material surface and the water drop. In this case, a contact angle of 90° or more indicates hydrophobicity. Accordingly, a water drop was applied on a surface of each skull replacement material prepared in Example 1-1, and then, the contact angle between each material surface and the water drop was measured to generate results, as shown in FIG. 3, that agarose, glass, and PET had a contact angle of 14.0°, 51.7°, 78.6°, respectively, which indicate hydrophilicity, whereas silicone and PDMS respectively had a contact angle of 95.1°, and 99.9°, which were 90° or more, indicating hydrophobicity.

Figure 4:
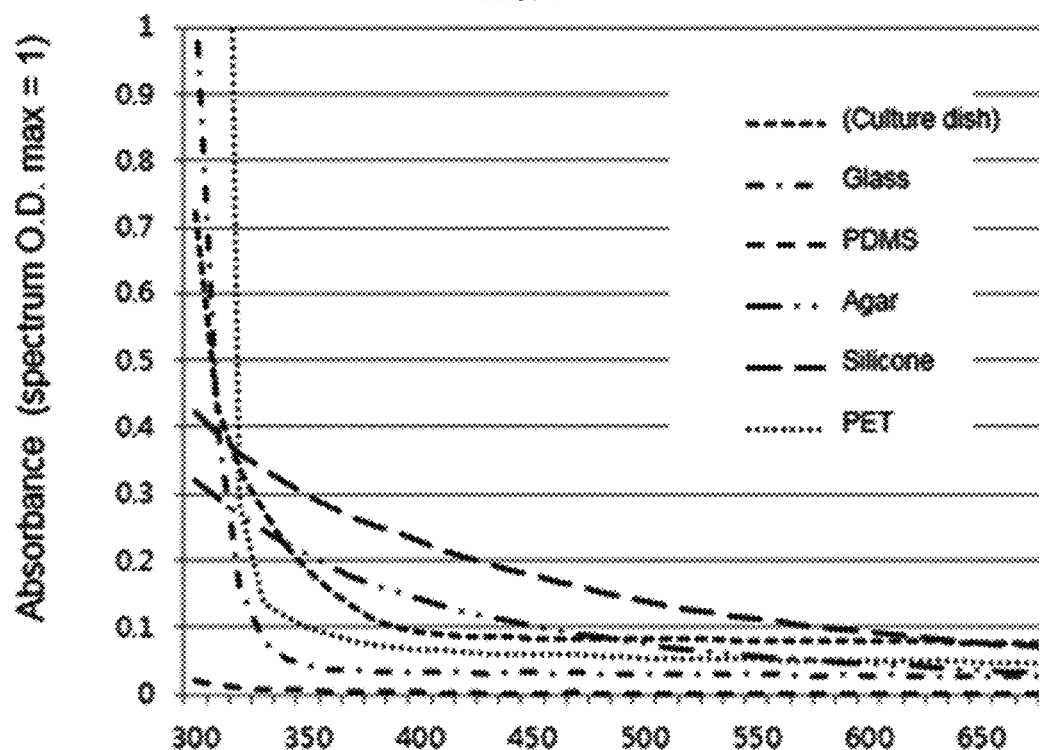
FIG. 4 shows the results of evaluating the transparency of each candidate material for a partial skull replacement, where the transparency was determined based on absorbance at wavelengths ranging from 300 nm to 700 nm.

In addition, the transparency was determined by measuring absorbance at wavelengths ranging from 300 nm to 700 nm, and an absorbance measured close to 0 indicates high transparency. Accordingly, the absorbance of each material was measured at wavelengths ranging from 300 nm to 700 nm, and as shown in FIG. 4, only PDMS among the skull replacement materials had an absorbance close to 0 over the entire wavelength range of 300 nm to 700 nm and was found to be a material having high and uniform transparency.

1-4. Ultrasound Transmission Properties

Reducing the loss of ultrasound by reflection is very important when the use of ultrasound is intended. That is, a difference in acoustic impedance (Z) between two different materials results in ultrasound reflection at the interface, and the larger the reflection is, the lower the ultrasonic transmittance becomes, and the material becomes less adequate as a cranial window. An acoustic reflection coefficient (R) is proportional to the square of the difference in acoustic impedance ($Z_1$ and $Z_2$) between two materials and is represented by the following equation:

$$R=(Z_2-Z_1)^2/(Z_2+Z_1)^2$$

Therefore, it is required to use a window having an acoustic impedance similar to that of brain tissue or CSF to reduce the loss of ultrasound by reflection.

Among candidate materials for a partial skull replacement prepared according to Example 1-1, PDMS has an acoustic impedance of 1.04 Rayl (or, 1.04 kg/($m^2$·sec)) that is close to the acoustic impedance of brain tissue (1.6 Rayl) and water (1.48 Rayl), and, the reflection corresponds to be 3 to 5% when the PDMS is in contact with these materials. In contrast, glass has an acoustic impedance of 12.3 MRayl, which results in pronounced impedance mismatch and thus the large reflection of 59% when brought into contact with brain tissue. In addition, when ultrasound is used for imaging, the ultrasound experiences reflection twice at the entering and exiting interfaces of the window. The loss of the ultrasound increases even more when glass is used for the window. As a result, when the realization of ultrasound imaging or treatment from outside the window is intended, the use of PDMS can achieve a significantly low loss of ultrasound by reflection as compared to when conventional glass is used.

In addition, when ultrasound passes through PDMS, the ultrasonic attenuation within the PDMS medium increases with the ultrasound operation frequency and the thickness of PDMS. The ultrasonic attenuation in the frequency band (<10 MHz) typically used for the imaging and treating of a living body is well known, and, based on PDMS with 1-mm thickness, ultrasound propagation through the PDMS film results in 1-dB attenuation for 3-MHz frequency, and 3-dB attenuation for 9-MHz frequency [Tsou et al., Ultrasound Med. Biol. 34, 963 (2008)]. When PDMS is selected as the skull replacement material, a cranial window typically having a small thickness of about 0.1 to 0.2 mm can be easily prepared, and ultrasonic attenuation significantly lower than the aforementioned attenuation value can be realized.

To summarize the results, PDMS, which has little cytotoxicity, high transparency, and acoustic impedance matching with brain tissues or CSF, was confirmed to be most appropriate as the skull replacement material for the long-term monitoring of a brain surface within the skull. Therefore, in the following examples, tests were carried out by using PDMS as the skull replacement material.

Example 2

Preparation of Window by Attaching Artificial Skull Substitute

The present inventors intended to apply PDMS, which was selected to be most appropriate as the skull replacement material according to the above Example 1, to the skull of a rat.

Figure 5:
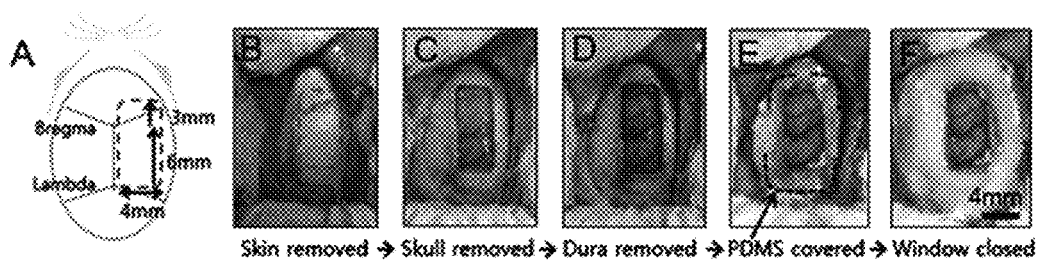
FIG. 5 illustrates a process of preparing a window by removing the skull of a rat and attaching an artificial partial skull replacement consisting of PDMS to the same area.

As appears in FIG. 5, skin in the area corresponding to biological tissues to be observed by visualization was removed to cause the skull to be exposed (blue dot lines in FIG. 5A and FIG. 5B), and then, the skull was removed with a drill (FIG. 5C) to exposure brain under the skull. Then, meninges on the cortex was removed with a pair of fine forceps, and, before the brain expanded as a result of the removal of meninges, an artificial partial skull replacement consisting of PDMS with an appropriate thickness was applied on the cortical tissue, and attached, with an instant glue, to the skull in the affected area (FIG. 5D and FIG. 5E). Lastly, a dental resin was used to seal and cover all of the connection between the artificial partial skull replacement and the bone to form a tightly closed window and achieve the stable cranial window which is the integration of the artificial partial skull replacement and the rat skull (FIG. 5F).

Example 3

Figure 6:
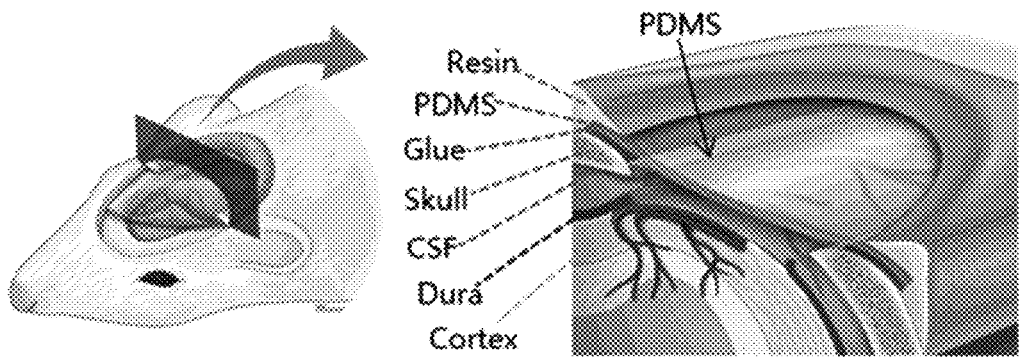
FIG. 6 is a cross-sectional view schematically showing a cross-section of the skull to which an artificial partial skull replacement consisting of PDMS was attached.

Confirmation of Excellence of Artificial Skull Substitute in Biological Tissue Monitoring A cross-section of the skull to which the artificial partial skull replacement is attached according to Example 2 is provided the schematics in FIG. 6. As shown in FIG. 6, the artificial partial skull replacement cranial window of the present invention has a flexible form, which enables the partial skull replacement to be attached to the skull of a rat for the long-term monitoring of the brain and a biological structure within the skull in real time. The following experiments were conducted with the intention of confirming the above statement.

3-1. Evaluation of Stability of Brain Surface Tissues and Blood Vessels

Figure 7:
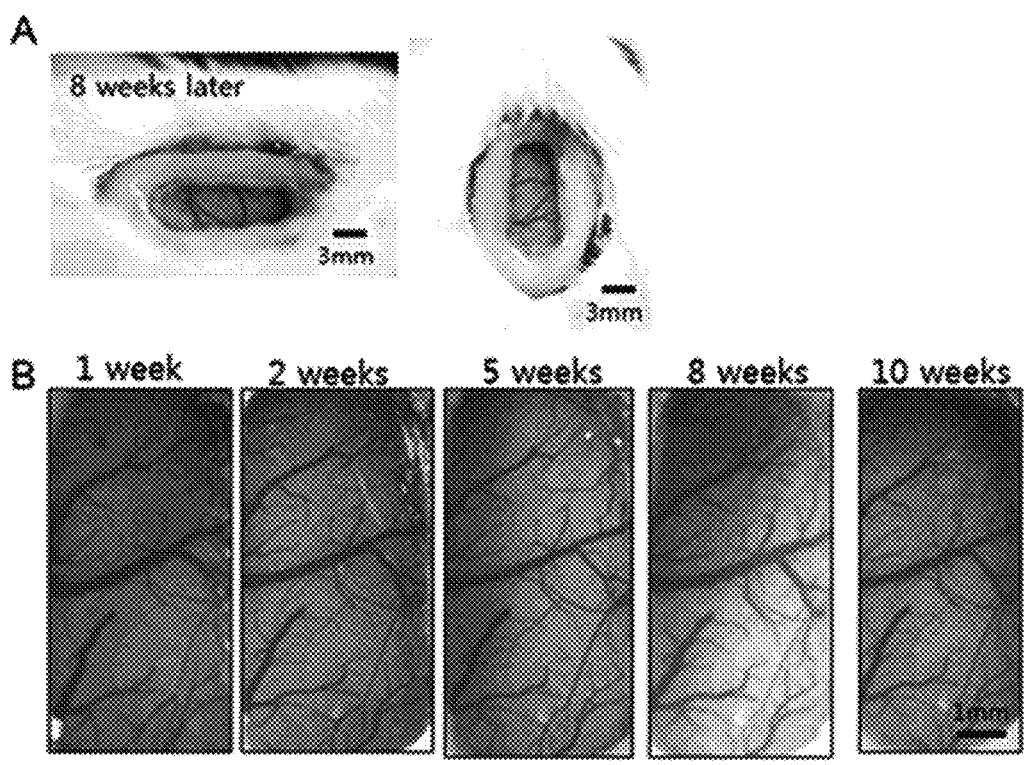
FIG. 7 shows (A) the affected area observed by the naked eye 8 weeks after the attachment of an artificial partial skull replacement; and (B) blood vessels and brain tissue within the skull observed over time (1 week, 2 weeks, 5 weeks, 8 weeks, and 10 weeks) through the artificial partial skull replacement.

Brain tissue and blood vessels within the skull were monitored for any change for a long period of 10 weeks from the day the artificial partial skull replacement was attached. As shown in FIG. 7, the results show that conditions enabling the observation of brain surface within the skull through the artificial partial skull replacement were maintained even after 8 weeks had elapsed (FIG. 7A) and confirmed that such observation is possible with high clarity more than 10 weeks through the optical imaging of blood vessels within the skull (FIG. 7B).

Figure 8:
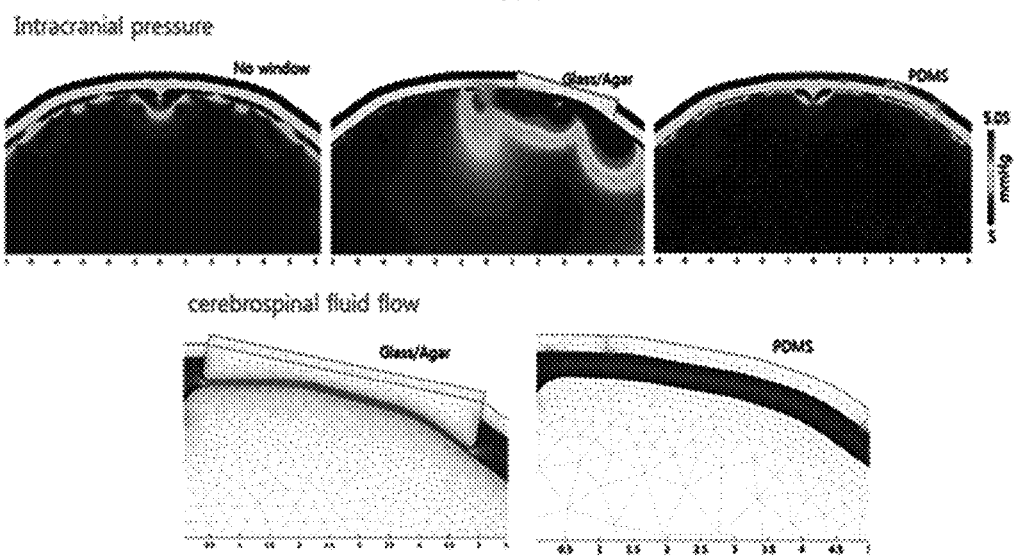
FIG. 8 shows an artificial skull bone and conventional glass/agar that were compared to each other, by simulation, in terms of intracranial pressure and a cerebrospinal fluid (CSF) flow.

In addition, to prove the excellence of the present invention, which enables the long-term monitoring of the brain and a biological structure within the skull, changes in intracranial pressure and CSF flow caused by each of the artificial partial skull replacement of the present invention and conventional glass/agar were compared. The result as shown in FIG. 8 specifically confirms, by simulation, that the artificial partial skull replacement of the present invention did not result in large changes in CSF flow and intracranial pressure, in contrast to conventional glass/agar, which greatly increased intracranial pressure within the skull due to the solidity of glass and blocked CSF flow. The result indicates that, by having a high degree of flexibility, the artificial skull bone consisting of PDMS can have a minimal influence on intracranial pressure to enable the stable monitoring of the brain and a biological structure within the skull for a long period of time.

3-2. Observation of Blood Flow Changes in Brain

Figure 9:
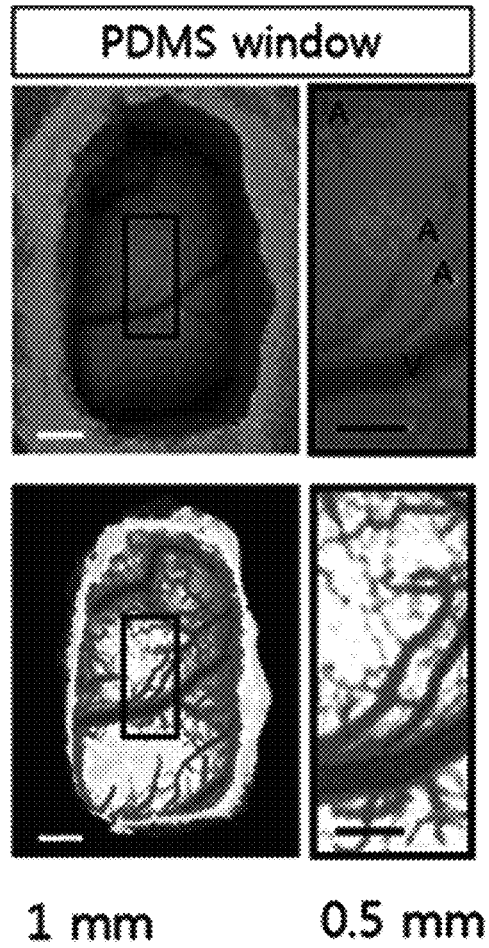
FIG. 9 shows blood flow images produced by laser speckle photography performed on a mouse to which an artificial partial skull replacement was attached.

Real-time changes in the brain blood flow of a rat (5 weeks post-implantation) to which the artificial partial skull replacement of the present invention was attached were measured by laser speckle photography. As appears in FIG. 9, it was found that the blood flow in blood vessels shown in a raw intensity image (FIG. 9, upper) was clearly seen red with high intensity (FIG. 9, lower). The result indicates that the use of an artificial partial skull replacement consisting of PDMS enables the real-time observation of changes in brain blood flow within the skull with enhanced effectiveness.

3-3. Monitoring of Brain Using Ultrasound

Figure 10:
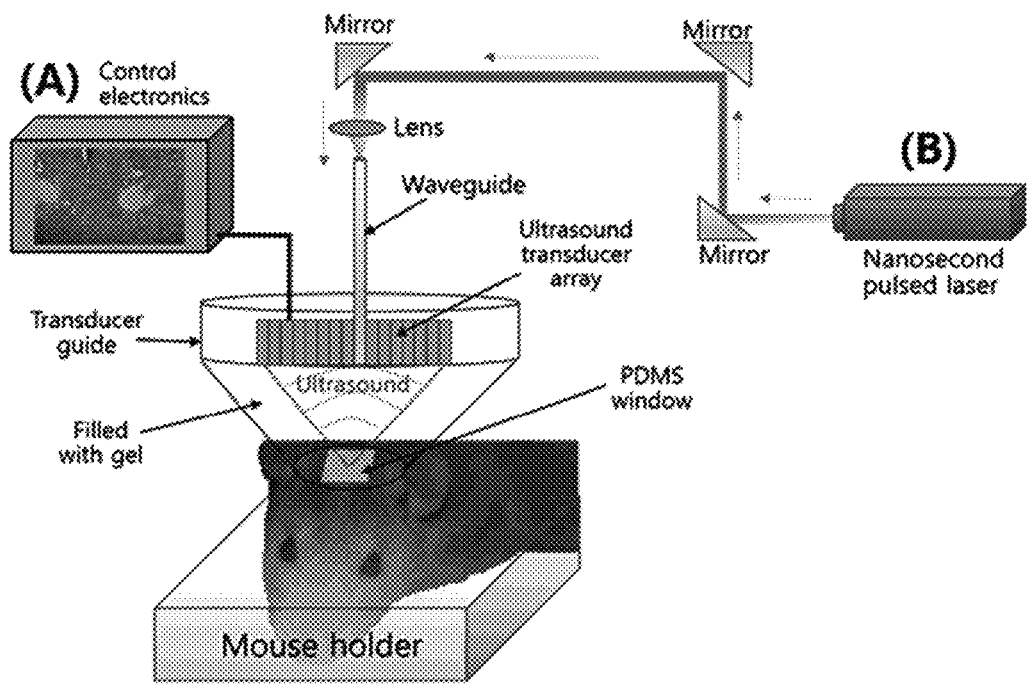
FIG. 10 is a schematic diagram for the use of ultrasound delivered through PDMS for visualization of an interior of the skull and therapeutic treatment.

FIG. 10 is a schematic diagram showing a rat to which the flexible artificial partial skull replacement of Example 2 and an ultrasound system were connected. As shown in FIG. 10, an electronic system (control electronics) marked as (A) on the left-hand side of the diagram may be used to operate an ultrasound transducer, and the transducer located in the center controls ultrasonic oscillation and measures ultrasound. Examples of the ultrasound transducer may include an array or a single-type device. The ultrasound oscillated from a surface of the transducer passes through a gel filling an area surrounding the transducer and subsequently passes through a PDMS window and then is delivered to CSF and brain tissues, and when the ultrasound travels through the above path, more than 50% of the ultrasound intensity (the wavelength of 3 MHz is assumed) radiated from the transducer surface can effectively reach the brain tissue. The ultrasound reflected back from the target site can be once again measured with the transducer producing an image, and, when therapeutic treatment is intended, high-intensity focused ultrasound can be delivered to the target site to destroy the tissue, causing mechanical disturbance, or the like.

In addition, (B) on the right-hand side of the diagram may be used for a photoacoustic imaging purpose. A waveguide for the delivery of light to the central portion is installed in a central part of the transducer to induce the direct incidence of a nanosecond pulse laser into the brain, in which case, the laser beam passes through the transparent PDMS window and reaches the target site in the brain. The absorbed pulse laser beam results in photoacoustic ultrasound generated from the brain, and such ultrasound once again passes through the PDMS window and reaches the transducer. The measured ultrasound can be produced into an image by the control electronics.

Example 4

Confirmation of Excellence of Artificial Skull Substitute in Delivery of Agent into Biological Tissues The following experiments were carried out with the intention to demonstrate the feasibility of a direct delivery of a foreign substance into brain tissues through the artificial partial skull replacement of the present invention and the repetitive administration of the foreign substance.

4-1. Imaging of Brain Tissues

First, the artificial partial skull replacement of the present invention was attached to the skull of a transgenic mouse expressing green fluorescence for microglia, and the brain tissues of the living mouse was produced into an image by an in-vivo multi photon confocal laser microscope that uses a laser.

Figure 11:
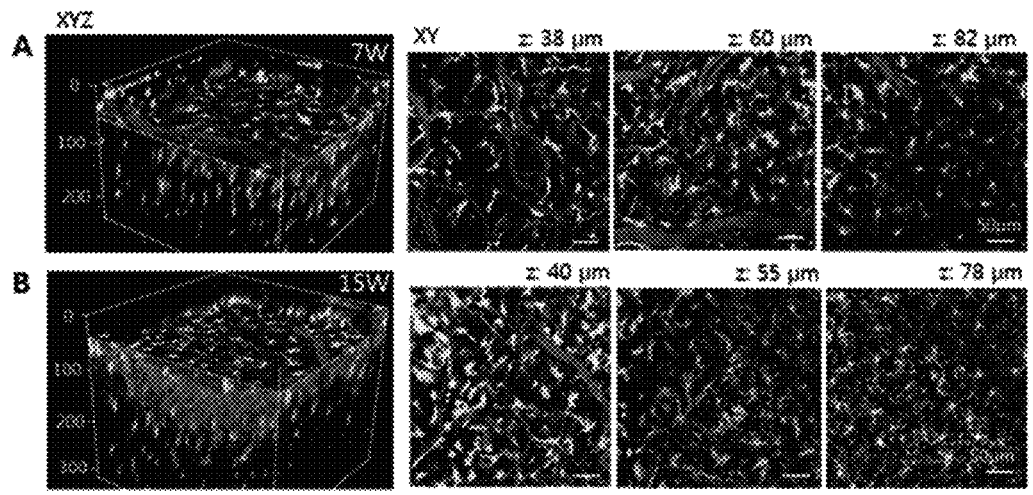
FIG. 11 shows the results confirming that laser transmission and fluorescence imaging were continued without an issue even after a prolonged use of the window, where the results were obtained (A) 7 weeks and (B) 15 weeks, respectively, after the attachment of an artificial partial skull replacement to a transgenic mouse ($Cx3Cr1^{GFP+/-}$ Tg mouse) expressing fluorescence marker for microglial cell, by clearly visualizing blood vessels and microglial cells under a multi photon confocal laser microscope.

As shown in FIG. 11, blood vessels (red), into which dextran was injected, and microglial cells (green) were identified in mice at 7 weeks and 15 weeks, respectively, after the attachment of the artificial partial skull replacement, which specifically indicated that microglial cells were well distributed in the area surrounding blood vessels and that a healthy immune status was maintained.

Figure 12:
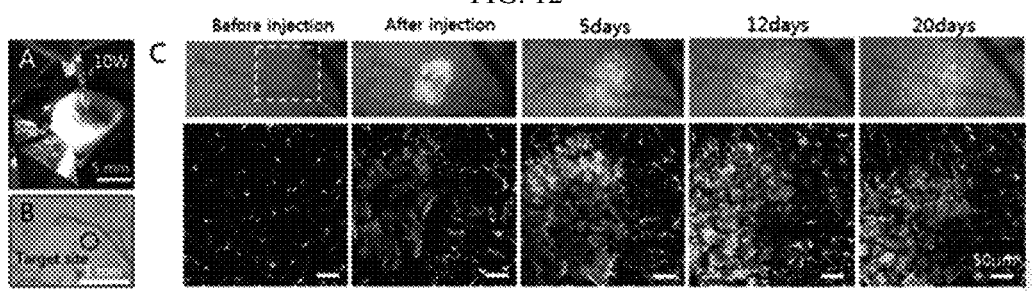
FIG. 12 shows the results of repeated imaging, performed over 20 days, of a microglial cell reaction after a surgery for implanting an artificial partial skull replacement into a transgenic mouse expressing microglial fluorescence protein and the subsequent injection of a red fluorescence protein directly into brain tissues.

Additionally, after surgically providing an artificial partial skull replacement to a transgenic mouse expressing green fluorescence for microglia, a hydrogel protein marked with a red fluorescent protein was directly injected into brain tissue through a glass pipette, and the reactions of microglial cells were monitored through repetitive in-vivo multi photon confocal imaging over 20 days (FIG. 12) through the partial skull replacement cranial window with PDMS.

4-2. Measurement of Brain Tissue Signals

After the attachment of the artificial partial skull replacement of the present invention, the functions of brain tissue were measured in real time.

Figure 13:
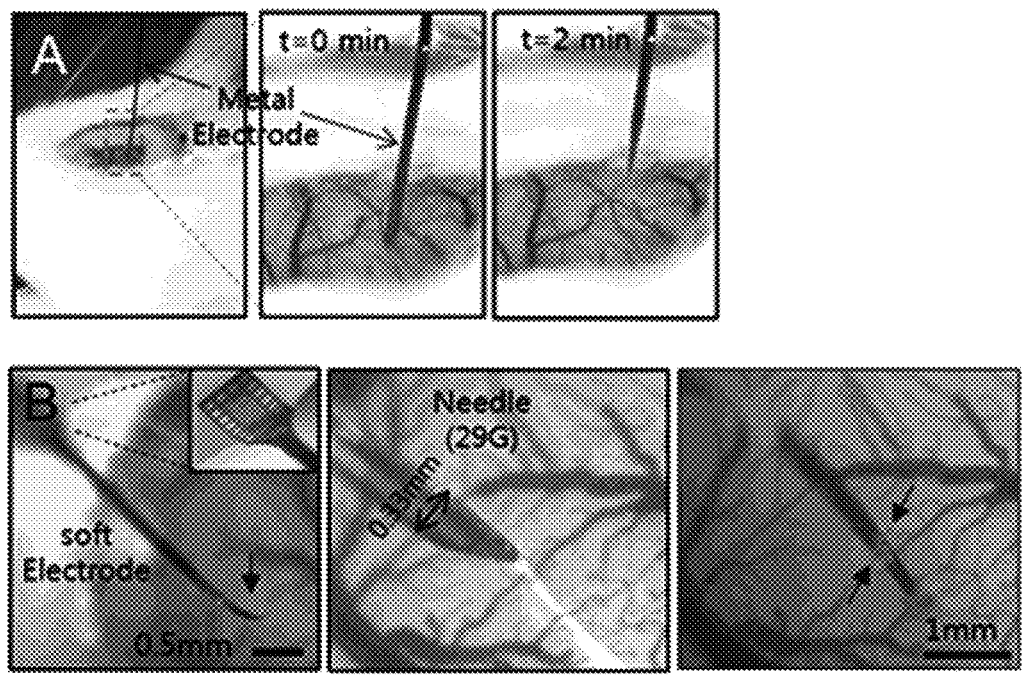
FIG. 13 is experimental results showing the feasibility of the insertion of (A) a hard metal electrode and (B) a soft electrode through the artificial partial skull replacement attached to a part of skull of a rat, wherein the electrodes are for measuring a neuronal signal.

First, when the feasibility of the direct penetration of an electrode for measuring brain signals into brain tissues through the artificial partial skull replacement of the present invention was tested, it was found that various electrodes (FIG. 13A: metal electrode, FIG. 13B: soft electrode) could penetrate through the artificial partial skull replacement, as shown in FIG. 13.

Figure 14:
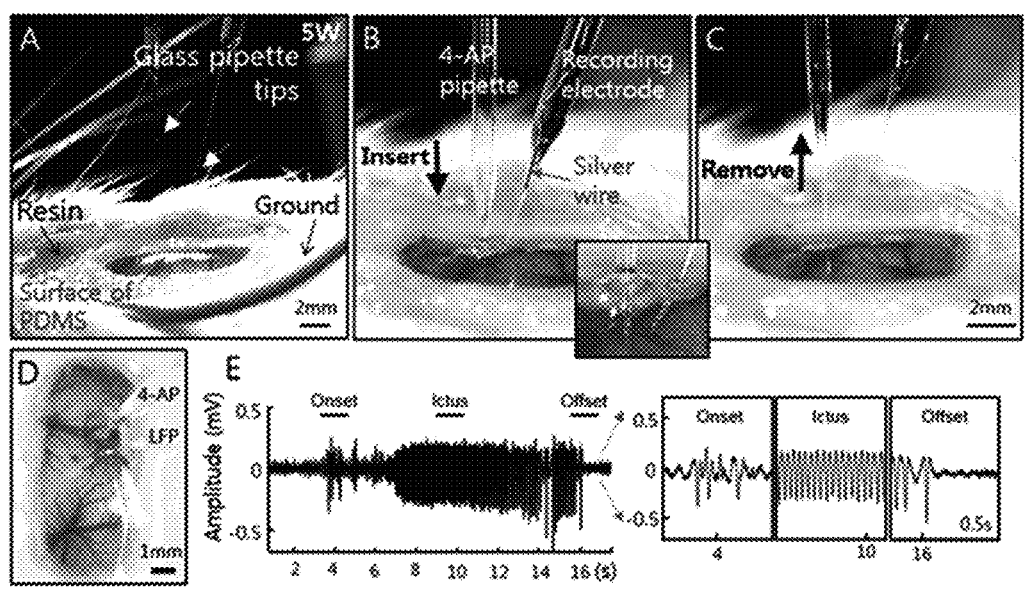
FIG. 14 shows, for the real-time monitoring of brain tissue functionality, (A) and (B) a process of inserting a glass pipette through an artificial partial skull replacement cranial window, (C) the appearance of the artificial partial skull replacement observed by the naked eye after the removal of the pipette, (D) the location on the artificial partial skull replacement where the penetration of the glass pipette took place, and (E) a result of monitoring changes in cranial nerve signals caused by the administration of a drug, 4-aminopyridine (4-AP), and analyzing the brain signal patterns.

Next, to measure the functionality of brain tissue, two glass pipettes were inserted into an artificial partial skull replacement consisting of PDMS, as shown in FIG. 14A and FIG. 14B. One of the glass pipettes was for injecting 4-aminopyridine (4-AP), a potassium channel blocker, which is a drug for inducing epilepsy, and the other was a pipette containing an electrode for brain signal measurement. As appears in FIG. 14D, it was found that the glass pipette penetrated through the artificial partial skull replacement.

Next, when the brain signals were measured, a local field potential (LFP), which is a signal indicating epilepsy induced by 4-AP, was detected as shown in FIG. 14E.

Next, even when the pipette was removed after the brain signal measurement, the artificial partial skull replacement of the present invention remained intact, without leaving any traces, as shown in FIG. 14C.

The results of using an artificial partial skull replacement consisting of PDMS indicate the possibility of a direct, repetitive, and long-term administration of various foreign substances into a single animal, which leads to the direct observation of changes in brain tissue functionality by a penetration method, which has been impossible to carry out by far. Also indicated is the feasibility of conducting an experiment on a living animal repetitively for an extended period of time, because the artificial structure remains intact even after the experiment.

The above description of the invention is only exemplary, and it will be understood by those skilled in the art that various modifications can be made without departing from the scope of the present invention and without changing essential features. Therefore, the above-described examples should be considered in a descriptive sense only and not for the purposes of limitation.

What is claimed is:

1. A method of preparing a window in a skull, the method consisting of:
    removing the skull in a target site;
    disposing a partial skull replacement consisting of polydimethylsiloxane (PDMS) in an area from which the skull was removed; and
    sealing a connection between the skull and the partial skull replacement,
    wherein the method is characterized by minimalizing influence of a flow of cerebrospinal fluid and an intracranial pressure in the skull.

2. The method of claim 1, wherein the target site includes cerebral blood vessels or brain cells.

3. The method of claim 1, wherein the sealing comprises applying a dental resin between the skull and the partial skull replacement.

4. A method of monitoring biological tissues within a skull, the method consisting of:
    removing the skull in an area to be monitored;
    disposing a partial skull replacement consisting of polydimethylsiloxane (PDMS) in the area from which the skull was removed;
    sealing a connection between the skull and the partial skull replacement; and
    monitoring the biological tissues within the skull through the disposed partial skull replacement,
    wherein the method is characterized by minimalizing influence of a flow of cerebrospinal fluid and an intracranial pressure in the skull.

5. The method of claim 4, wherein the monitoring is carried out using a laser or ultrasound.

6. The method of claim 4, wherein the sealing comprises applying a dental resin between the skull and the partial skull replacement.

7. A method of injecting an agent into a skull, the method consisting of:
    removing the skull in an area of injection;
    disposing a partial skull replacement consisting of polydimethylsiloxane (PDMS) in an area from which the skull was removed;
    sealing a connection between the skull and the partial skull replacement;
    penetrating the partial skull replacement with an injection tool; and
    injecting the agent into the skull via the injection tool that has penetrated the partial skull replacement,
    wherein the method is characterized by minimalizing influence of a flow of cerebrospinal fluid and an intracranial pressure in the skull.

8. The method of claim 7, wherein the agent is a lesion inducer, a therapeutic agent, a treatment promoter, a diagnostic agent, or an imaging agent.

9. The method of claim 7, wherein the injection tool is a pipette or a needle.

10. The method of claim 7, wherein the sealing comprises applying a dental resin between the skull and the partial skull replacement.

* * * * *